US010428376B2

(12) United States Patent
Hajeri et al.

(10) Patent No.: US 10,428,376 B2
(45) Date of Patent: Oct. 1, 2019

(54) RNA AMPLIFICATION AND OLIGONUCLEOTIDE LIBRARY PREPARATION

(71) Applicant: REGENTS OF THE UNIVERSITY OF MINNESOTA, Minneapolis, MN (US)

(72) Inventors: Praveensingh B. Hajeri, Falcon Heights, MN (US); Subbaya Subramanian, Roseville, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 177 days.

(21) Appl. No.: 15/100,784

(22) PCT Filed: Dec. 2, 2014

(86) PCT No.: PCT/US2014/068087
§ 371 (c)(1),
(2) Date: Jun. 1, 2016

(87) PCT Pub. No.: WO2015/084802
PCT Pub. Date: Jun. 11, 2015

(65) Prior Publication Data
US 2016/0304947 A1    Oct. 20, 2016

Related U.S. Application Data

(60) Provisional application No. 61/910,603, filed on Dec. 2, 2013.

(51) Int. Cl.
*C12Q 1/6855* (2018.01)
*C12Q 1/6834* (2018.01)
*C12Q 1/6837* (2018.01)

(52) U.S. Cl.
CPC ......... *C12Q 1/6855* (2013.01); *C12Q 1/6834* (2013.01); *C12Q 1/6837* (2013.01)

(58) Field of Classification Search
CPC .................................................. C12Q 1/6855
USPC .......................................................... 506/9
See application file for complete search history.

(56) References Cited

U.S. PATENT DOCUMENTS

2003/0202980 A1*  10/2003  Caplan et al.
2006/0019298 A1*   1/2006  Shima ................ C12N 15/1096
                                                      435/6.1
2007/0011120 A1*   5/2007  Cao et al.
2011/0195457 A1*   8/2011  Nelson et al.

FOREIGN PATENT DOCUMENTS

WO    WO 2006/003721 A1    1/2006

OTHER PUBLICATIONS

Bergemann et al. (Journal of Magnetism and Magnetic Materials, 194, 1999, pp. 45-52). (Year: 1999).*
"AGENCOURT® RNAClean® XP. In Vitro Produced RNA and cDNA Purification," Jan. 1, 2009, pp. 1-14. Retrieved from the Internet: URL:http://www.beckmancoulter.de/beckman2_media/LifeSciences/Produkte/Instrumente/Molekularbiolgie/DNARNA_Aufreinigung/DNA_Aufreinigung/Apps_RNACleanXP/RNAClean XP_Protokoll.pdf (Retrieved on Feb. 12, 2015).
"AGENCOURT® AMPure® XP PCR Purififcation," Jan. 1, 2009, pp. 1-9. Retreived from the Internet: URL:http://nextgen.mgh.harvard.edu/attachments/AMPureXPProtocol_000387v001.pdf (Retrieved on Feb. 12, 2015).
Axtell, M.J., "Classification and comparison of small RNAs from plants," *Annu Rev Plant Biol*, 2013;64:137-59.
Castel and Martienssen, "RNA interference in the nucleus: roles for small RNAs in transcription, epigenetics and beyond," *Nat Rev Genet*, Feb. 2013;14(2):100-112.
DeAngelis et al., "Solid-phase reversible immobilization for the isolation of PCR products," *Nucleic Acids Res*, 1995;23(22):4742-4743.
"Epicentre® MasterPure™ DNA Purification Kit," Jan. 1, 2012, pp. 1-13, Retrieved from the Internet:URL:http://www.epibio.com/docs//default-source/protocols/masterpure-dna-purification-lit.pdf?sfvrsn=6. (Retrieved on Feb. 10, 2015).
Gill et al., "Nucleic Acid Isothermal Amplification Technologies—A Review," *Nucleosides, Nucleotides, and Nucleic Acids*, Taylor & Francis, Mar. 1, 2008;27(3):224-243.
Harbers et al., "The current status of cDNA cloning," *Genomics*, Jan. 28, 2008;91(3):232-242.
Hawkins et al., "DNA purification and isolation using a solid-phase," *Nucleic Acids Res*, Oct. 25, 1994;22(21):4543-4544.
International Search Report and Written Opinion for PCT/US2014/068087, issued by the European Patent Office, dated Mar. 31, 2015; 15 pgs.
International Preliminary Report on Patentability for PCT/US2014/068087, issued by the International Bureau of WIPO, dated Jun. 16, 2016; 9 pgs.
Kim et al., "Biogenesis of small RNAs in animals," *Nat Rev Mol Cell Biol*, Feb. 2009; 10(2):126-139.
Kurn et al., "Novel Isothermal, Linear Nucleic Acid Amplification Systems for Highly Multiplexed Applications," *Clinical Chem*, Oct. 1, 2005;51(10):1973-1981.
Paithankar et al., "Precipitation of DNA by polyethylene glycol and ethanol," *Nucleic Acids Res*, Mar. 25, 1991;19(6):1346.
Riedel et al., "Genomics and Physiology of a Marine Flavobacterium Encoding a Proteorhodopsin and a Xanthorhodopsin-Like Protein," *PLOS One*, Mar. 4, 2013;8(3):e57487.
Schmitz et al., "Purification of nucleic acids by selective precipitation with polyethylene glycol 6000," *Analytical Biochem*, Jul. 15, 2006;354(2):311-313.

(Continued)

*Primary Examiner* — Karla A Dines
(74) *Attorney, Agent, or Firm* — Mueting, Raasch & Gebhardt, PA

(57) ABSTRACT

This disclosure describes, in one aspect, a method of amplifying an RNA template. Generally, the method includes synthesizing an oligonucleotide from the RNA template, isolating at least a portion of the oligonucleotide, and subjecting the isolated product to treatment with an RNase and/or glycosylase.

15 Claims, 10 Drawing Sheets

(56) References Cited

OTHER PUBLICATIONS

Singh et al., "cDNA Cloning and Molecular Modeling of Procerain B, a Novel Cysteine Endopeptidase Isolated from *Calotropis procera*," *PLOS One*, Mar. 20, 2013;8(3):e59806.
Tan et al., "DNA, RNA, and Protein Extraction: The Past and The Present," *J of Biomed and Biotech*, Jan. 1, 2009;2009:1-10.
Wang et al., "A Low-Cost Library Construction Protocol and Data Analysis Pipeline for Illumina-Based Strand-Specific Mulitplex RNA-seq," *PLOS One*, Oct. 19, 2011;6(10):e26426.
Wang et al., "Multiplexed Strand-specific RNA-Seq Library Preparation for Illumina Sequencing Platforms," *PLOS One*, Oct. 19, 2011;6(10):e26426.

* cited by examiner

A

■ 2 ng Human Brain ■ 2 ng Universal Human Reference ■ DNA Ladder

B

A

B

C

D

A

B

A

B

A

B

A

B

A

B

ABSTRACT# RNA AMPLIFICATION AND OLIGONUCLEOTIDE LIBRARY PREPARATION

CROSS-REFERENCE TO RELATED APPLICATION

This application is the § 371 U.S. National Stage of International Application No. PCT/US2014/068087, filed 2 Dec. 2014, which claims priority to U.S. Provisional Patent Application Ser. No. 61/910,603, filed Dec. 2, 2013, each of which is incorporated herein by reference.

SUMMARY

This disclosure describes, in one aspect, a method of amplifying an RNA template. Generally, the method includes synthesizing an oligonucleotide from the RNA template, thereby producing a product that comprises a digestible or degradable oligonucleotide adapter, isolating at least a portion of the oligonucleotide, and subjecting the isolated product to treatment that digests at least a portion of the digestible adapter.

In some cases, isolating at least a portion of the oligonucleotide can involve performing isothermal amplification on at least a portion of the isolated oligonucleotide, then isolating at least a portion of the isothermal amplification product.

In some embodiments, the treatment that digests at least a portion of the digestible adapter can involve treatment with an RNase. In some of these embodiments, the RNase used to treat the isolated product can include RNase-A and/or RNase-H.

In some embodiments, the treatment that digests at least a portion of the digestible adapter can involve treatment with a glycosylase. In some of these embodiments, the glycosylase comprises uracil DNA glycosylase.

In some embodiments, the treatment that digests at least a portion of the digestible adapter can involve physical or chemical fragmentation and/or digestion of the isolated product.

In some embodiments, isolating a portion of the oligonucleotide can include incubating at least a portion of the oligonucleotide in a composition that can include NaCl or KCl.

In some embodiments, isolating a portion of the oligonucleotide can include incubating at least a portion of the oligonucleotide in a composition that can include $MgCl_2$, $MgSO_4$, or $(CH_3COO)_2Mg$.

In some embodiments, isolating a portion of the oligonucleotide can include incubating at least a portion of the oligonucleotide in a composition that can include polyethylene glycol.

In some embodiments, isolating a portion of the oligonucleotide can include incubating at least a portion of the oligonucleotide in a composition that can include ethanol.

In some embodiments, isolating a portion of the oligonucleotide can include incubating at least a portion of the oligonucleotide in a composition that can include isopropanol (2-propanol).

In some embodiments, isolating a portion of the oligonucleotide can include incubating at least a portion of the oligonucleotide in a composition that can include isobutanol (2-Butanol).

In another aspect, this disclosure describes a method of preparing a library of polynucleotides. Generally, the method includes obtaining a sample comprising a plurality of polynucleotides, shearing the plurality of polynucleotides, thereby producing a plurality of polynucleotides fragments, treating the plurality of polynucleotides or the plurality of polynucleotide fragments with an RNase and/or DNA glycosylase, repairing the ends of polynucleotide fragments with an enzyme, ligating a first polynucleotide fragment into a first adapter, and ligating a second polynucleotide fragment into a second adapter.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
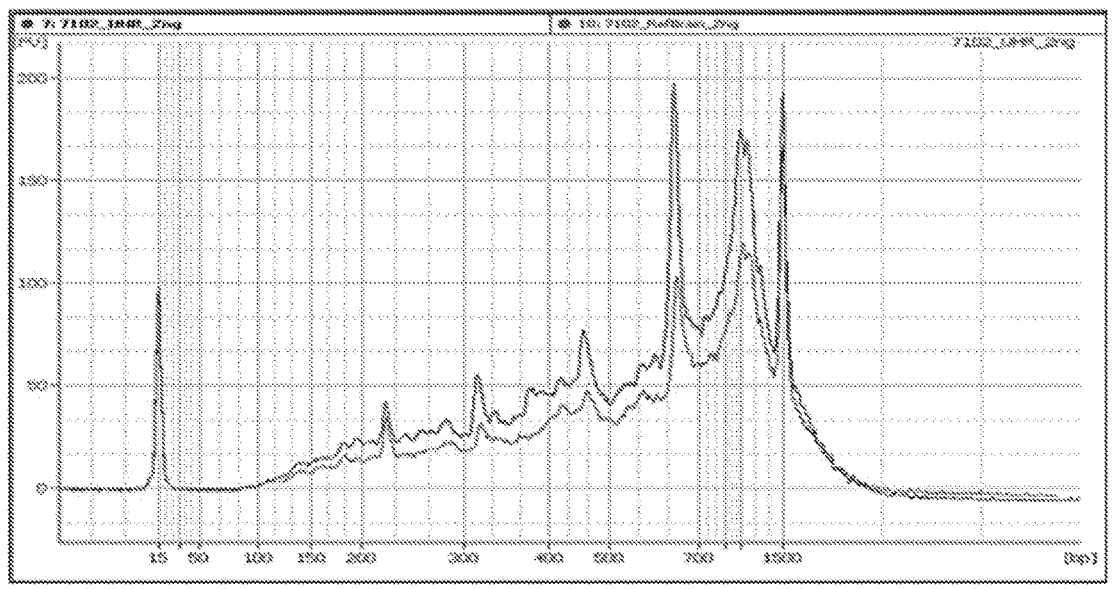
FIG. 1. Data comparing DNA amplification and recovery by existing methods and methods described herein. (A) Agilent DNA 1000 labchip assay profile of RNA amplification product using OVATION RNA-seq system V2 (NuGEN Technologies, Inc., San Carlos, Calif.). The minimum fragment size seen is approximately 70 bp. (B) Similar profile of product of RNA amplification using our methods. Fragments of approximately 30 nucleotides (including adapters) and above were detected, confirming the recovery of both small and long RNAs in same amplification procedures.
Figure 1:
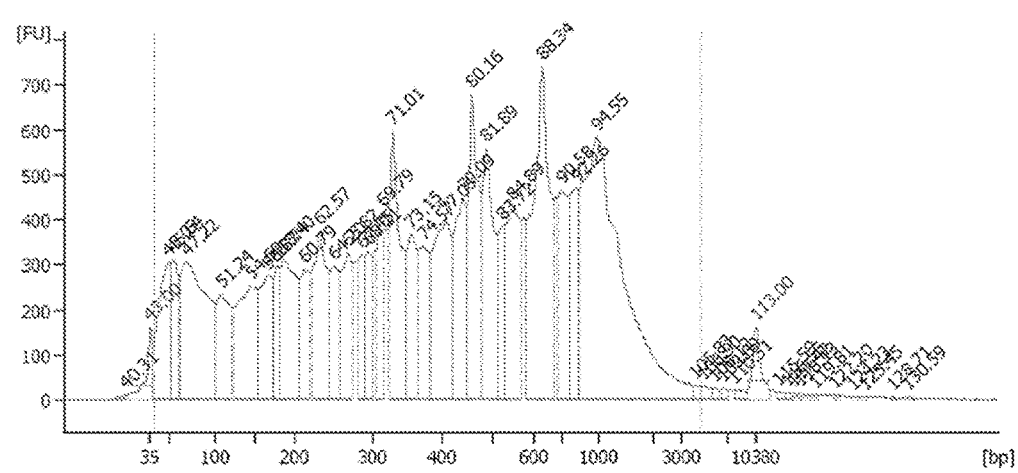

One way to study basic mechanisms of various biological and/or disease processes involves studying the expression of coding and/or non-coding RNAs. Non-coding RNAs can be involved in regulatory processes in various biological contexts. There are several types of non-coding RNAs of various lengths. For example, small RNAs such as miRNAs, endo-siRNAs, piRNAs, and rasi-RNAs can range from about 19-30 nucleotides, while snRNAs, Y-RNAs, riboswitches, snoRNAs can range from about 40-140 nucleotides. Each of these small RNAs can be involved in many cellular functions. Further, longer non-coding RNAs can range up to several kilobases in length.

In many diseases the RNA expression profile of normal cells is different than the RNA expression profile of diseased cells. Expression profiling can allow one to identify and/or recognize differences in RNA expression. Expression profiling can, therefore, contribute to analyses that may establish a cause and effect relationship between expression of a coding/non-coding RNA and a disease or developmental process. In many cases, the number of cells available for experiments can be limited to a very small number—e.g., from 1 to a few hundred cells—depending upon unique features of the cell type under investigation. For example, in many diseased tissues, the number of cells that trigger or directly contribute to a disease may be relatively small compared to the majority of cells in the diseased tissue, which may be only supporting or secondary cells. In such cases, processing the entire tissue can increase background noise as the expression profile of the supporting and/or secondary cells does not necessarily correspond to the few disease/progenitor cells and, therefore, may not correspond to the disease or condition being analyzed. The low number of cells actually triggering and/or directly contributing to a disease condition can yield very low quantities of DNA and RNA—e.g., on the order of from 10 pg to 5 ng.

Current amplification and library preparation methods have various limitations when used for transcriptome analysis of coding and/or non-coding RNAs using such limited quantities of RNA as template. Currently, there are no methods to profile RNAs of smaller sizes (e.g., less than ~100 nucleotides) with limited quantity of template RNA. Therefore, the roles of small RNAs in normal developmental processes and in various diseases have been difficult to study.

This disclosure describes a novel method for amplifying total RNA using very low quantity of total RNA as template. Further, this disclosure describes a method for efficiently preparing a library from the amplified RNA product compatible for high throughput sequencing and microarray studies. As used herein, the term "amplified RNA product" refers to the product of amplifying an RNA template. An "amplified RNA product" may or may not, therefore, include RNA. The amplified RNA product can be in the form of, for example, single-stranded RNA, double-stranded RNA, single-stranded DNA, or double-stranded DNA. These methods, either alone or in combination with one another, can allow one to study biological and/or disease processes involving a limited number of relevant cells.

RNA Amplification

The method of RNA amplification described herein can be used with as little as 10 picograms (pg) of template. In particular, the method can be used with low amounts of RNA template—e.g., up to about 5 nanograms (ng), but also may be used with samples that provide greater amounts of template. Moreover, the method can capture any RNA of at least about 15 nucleotides. Thus, the method can amplify small RNAs that otherwise can be difficult to amplify and profile (FIG. 1B). As used herein, the term "small RNA" refers to an RNA having no more than 200 bases. This represents a significant improvement over existing methods, which typically involve either using at least 50 ng of enriched small-RNA template in order to capture all small RNAs or capturing only those RNAs longer than about 75 bp when a total-RNA template concentration of 10 pg to 5 ng is used (FIG. 1A).

A limitation of performing experiments with a low quantity of template is bias for longer RNAs introduced in amplification steps. The methods described herein can reduce this bias by several folds compared to conventional RNA amplification methods. (FIG. 1). FIGS. 1-4 show successful amplification of RNAs ranging from approximately 15 nucleotides to several kilobases proportionately to the unamplified template. This, again, is a significant improvement over existing methods, which can show bias even for RNAs approximately as long as 75 nucleotides (FIG. 1A).

The methods described herein allow one to amplify RNAs having as few as, for example, 15 nucleotides using 10 pg to 5 ng of RNA as template and does so with negligible bias. Thus, the methods described herein are the first to be designed to amplify oligonucleotides from about 15 nucleotides to about 70 nucleotides with low bias.

While described and exemplified at various locations herein in the context of particular embodiments that involve the use of small RNAs, the methods described herein are equally capable of amplifying small and long RNAs and can do so simultaneously. Thus, the methods described herein allow one to prepare libraries of total RNA for downstream analytical applications that include small RNAs. Because the methods amplify small RNA and long RNA with negligible bias, one can amplify total RNA—i.e., both small and long RNAs—in a single process.

The RNA template amplified by the method described herein can include any suitable RNA template having no fewer than 15 nucleotides. Suitable RNA templates include, for example, single-stranded RNA, double-stranded RNA, a mixture of both single- and double-stranded RNAs, a DNA-RNA heteroduplex, a DNA-RNA hybrid, a single strand of oligonucleotide containing both ribose and de-oxy ribose nucleotides, any form of modified RNA/DNA, total RNA isolated from tissues/cells, or any other substance yielding RNA.

The amount of RNA template required as a starting material for amplification can be as little as 10 pg such as, for example, at least 10 pg, at least 25 pg, at least 50 pg, at least 100 pg, at least 250 pg, at least 500 pg, at least 1 ng, or at least 2 ng of RNA template.

Generally, the RNA amplification method can employ, with certain modifications, any conventional RNA amplification method. Suitable RNA amplification kits are available from, for example, New England Biolabs Inc. (Ipswich, Mass.), System Biosciences, Inc. (Mountain View, Calif.), Epicentre Biotechnologies Corp. (Madison, Wis.), and Invitrogen (Life Technologies, Grand Island, N.Y.). In some cases, the RNA amplification can further involve isothermal amplification such as, for example, single primer isothermal amplification (SPIA) such as, for example, Ovation RNA-Seq System V2 (NuGEN Technologies, Inc., San Carlos, Calif.).

Thus, in one embodiment, the RNA amplification method can include, generally, synthesizing cDNA from the RNA template, isolating at least a portion of the cDNA, performing SPIA amplification, thereby producing an SPIA product that comprises a digestible oligonucleotide adapter, isolating at least a portion of the SPIA product, and subjecting the isolated SPIA product to treatment that digests at least a portion of the digestible adapter. The resulting product can be used for quantitative and/or qualitative analysis.

While exemplified below in the context of amplification using the OVATION RNA-Seq System V2 (NuGEN Technologies, Inc., San Carlos, Calif.) amplification system, our methods may be performed with amplification product produced using any suitable kit and/or protocol. For example, the OVATION RNA-Seq System V2 (NuGEN Technologies, Inc., San Carlos, Calif.) is designed to minimize rRNA carryover. Other amplification kits from other manufacturers, however, may not have this feature. In those cases, the methods described herein can include an independent rRNA removal step using a conventional method before making a library for sequencing. Also, while described below in the context of synthesizing cDNA from an RNA template, the amplification product can alternatively include RNA.

The method described herein includes modifying, as described below, the isolation methods used to isolate cDNA synthesized from an RNA template and/or isolate RNA synthesized from an RNA template. The modifications permit one to isolate at least a portion of the cDNA synthesized from the RNA template without eliminating smaller sized products—e.g., products shorter than 200 nucleotides. The modifications allow isolation of both small RNAs (i.e., no more than 200 nucleotides) and long RNAs (i.e., greater than 200 nucleotides) that remain compatible with downstream enzymatic assay and/or analytical reactions. The modifications can result in more efficient recovery of the amplified product and/or maintain the suitability of the amplified product for use in downstream enzymatic assay and/or analytical reactions.

In an exemplary embodiment, one can isolate the synthesized cDNA using carboxyl-magnetic beads (e.g., Agencourt RNAClean XP beads or Agencourt AMPure beads, Beckman Coulter, Inc., Brea, Calif.) to isolate the second strand cDNA synthesis product. The ratio of carboxyl magnetic beads with respect to the quantity and/or volume of RNA/DNA (including, for example, DNA, RNA, a DNA/RNA hybrid, a heteroduplex, an oligonucleotide having at least one modified nucleotide) can vary up to about 10-fold. In some embodiments, the ratio of carboxyl magnetic beads to the quantity of RNA/DNA can be from about 1-fold to about 2-fold.

The isolation of the cDNA synthesis product can be improved by modifying the isolation step to use NaCl (or analogous salt such as, for example, KCl), $MgCl_2$ (or analogous salt such as, for example, $MgSO_4$ or $(CH_3COO)_2Mg$), polyethylene glycol (PEG, e.g., PEG-8000), ethanol, isopropanol, and/or isobutanol, either alone or in combinations. The particular conditions can depend, at least in part, on the components of earlier reaction buffers, other components of reaction, reaction products and templates.

The concentration of NaCl can vary up to 2.5 M. KCl may be used in similar manner. The total salt concentration can influence downstream reactions. Thus, the particular NaCl (or suitable analogous salt) concentration used in any particular application can be influenced, at least in part, by the concentration of other salts, if any, used in the isolation process. In particular embodiments, the concentration of NaCl (or suitable analogous salt) can be no more than 2.5 M such as, for example, no more than 2 M, no more than 1.5 M, no more than 1 M, no more than 500 mM, no more than 200 mM, or no more than 100 mM.

The concentration of $MgCl_2$, when used, can vary up to 1 M. Higher concentrations can improve the recovery of smaller fragments but also can affect downstream enzymatic reactions. Other salts of $Mg^{2+}$ such as, for example, $MgSO_4$, $(CH_3COO)_2Mg$ may be used in similar manner. The total salt concentration can influence downstream reactions. Thus, the particular $MgCl_2$ (or suitable analogous salt) concentration used in any particular application can be influenced, at least in part, by the concentration of other salts, if any, used in the isolation process. In particular embodiments, the concentration of $MgCl_2$ (or suitable analogous salt) can be no more than 1 M such as, for example, no more than 500 mM, no more than 100 mM, no more than 50 mM, no more than 20 mM, or no more than 10 mM.

The concentration (wt/volume) of polyethylene glycol can vary up to 30 percent. A higher concentration of PEG favors recovery of smaller fragments but may affect downstream applications. (Paithankar et al. 1991. *Nucleic Acids Res* 19(6):1346) The method can employ any polyethylene glycol having an average molecular weight of at least 200 (e.g., PEG 200) such as, for example, PEG 2000, 3000, 4000, 6000, 8000 and 20000.

In some embodiments, the concentration of ethanol can be a maximum of 80% (volume/volume) such as, for example, no more than 75%, no more than 70%, no more than 60%, no more than 50%, no more than 45%, no more than 40%, no more than 35%, no more than 30%, no more than 25%, no more than 20%, or no more than 15%. In some embodiments, the concentration of ethanol used can be a minimum of 10% (volume/volume) such as, for example, at least 15%, at least 20%, at least 25%, at least 30%, at least 40%, at least 45%, or at least 50%. In some embodiments, the concentration of ethanol can be expressed as a range having endpoints defined by any maximum ethanol concentration listed above and any minimum ethanol concentration listed above that is less than the maximum ethanol concentration. Thus, for example, in some embodiments, the ethanol concentration can be, for example, from about 15% to about 80%. Generally, using a higher concentration of ethanol can promote recovery of smaller fragments. In one exemplary embodiment, the ethanol concentration is 37%.

In some embodiments, the concentration of isopropanol can be a maximum of 50% (volume/volume) such as, for example, no more than 45%, no more than 40%, no more than 35%, no more than 30%, no more than 25%, no more than 20%, no more than 15%, or no more than 10%. In some embodiments, the concentration of isopropanol can be a minimum of 5% (volume/volume) such as, for example, at least 10%, at least 15%, at least 20%, at least 25%, at least 30%, at least 35%, or at least 40%. In some embodiments, the concentration of isopropanol can be expressed as a range having endpoints defined by any maximum isopropanol concentration listed above and any minimum isopropanol concentration listed above that is less than the maximum isopropanol concentration. Thus, for example, in some embodiments, the isopropanol concentration can be 10% to 50%. In other embodiments, the isopropanol concentration can be from 10% to 40%. Similar to ethanol, a higher concentration of isopropanol can promote recovery of smaller fragments.

In some embodiments, the concentration of isobutanol can be a maximum of 50% (volume/volume) such as, for example, no more than 45%, no more than 40%, no more than 35%, no more than 30%, no more than 25%, no more than 20%, no more than 15%, or no more than 10%. In some embodiments, the concentration of isobutanol can be a minimum of 5% (volume/volume) such as, for example, at least 10%, at least 15%, at least 20%, at least 25%, at least 30%, at least 35%, or at least 40%. In some embodiments, the concentration of isobutanol can be expressed as a range having endpoints defined by any maximum isobutanol concentration listed above and any minimum isobutanol concentration listed above that is less than the maximum isobutanol concentration. Thus, for example, in some embodiments, the isobutanol concentration can be 10% to 50%. In other embodiments, the isobutanol concentration can be from 10% to 40%. Similar to ethanol, a higher concentration of isobutanol can promote recovery of smaller fragments.

In one embodiment, for example, the synthesis product, whether cDNA or RNA, can be isolated using a composition that includes 10 mM NaCl, 20 mM $MgCl_2$, 5% PEG 8000, and 37% ethanol. In other embodiments, however, the synthesis product may be isolated using a composition that includes 5% PEG 8000 and 37% ethanol. In still other embodiments, the synthesis product may be isolated using a composition that includes 37% ethanol.

Thus, to improve the recovery of smaller fragments, one can isolate the cDNA synthesis product by incubating the product with a composition that includes one or more of: NaCl (or comparable salt), $MgCl_2$ (or comparable salt), PEG, ethanol, or isopropanol. The incubation may be performed at, for example, room temperature for a suitable time to allow the cDNA synthesis product to bind to the magnetic beads. Exemplary incubation times include, for example, an incubation of from one minute to many hours. In many embodiments, the incubation period can be from about 5 minutes to about 30 minutes.

The methods described herein also include subjecting the isolated product to treatment that digests at least a portion of the digestible adapter that is produced as a result of the amplification step. The isolated product may be cDNA prepared from the RNA template by any method including, for example, any of the methods described above. In particular, the isolated product may be cDNA that has been prepared with or without using isothermal amplification.

The digestible adapter may be subjected to enzymatic, physical, or chemical treatment. The particular treatment used may depend, at least in part, on the nature of the digestible adaptor on the amplification product and, therefore, depend at least in part on the particular method used to amplify the RNA template. For example, some digestible adapters may be susceptible to degradation by an RNase such as, for example, RNase-A or RNase-H. Other adaptors may be susceptible to degradation by a glycosylase such as, for example, uracil-DNA glycosylase. Still other adapters may be susceptible to degradation by physical (e.g., temperature, radiation, etc.) or chemical (e.g., acid hydrolysis) treatments. Digestion of the adapter may be performed before or after the amplified product is at least partially isolated. Thus, digestion of the adapter can include treating the amplified product, regardless of whether the amplified product is at least partially isolated.

In embodiments in which the digestible adapter is digested by treatment with an RNase, one can use any RNase that can degrade RNA in single-stranded RNA, double-stranded RNA, a RNA-DNA hybrid, a RNA-DNA hetero-duplex, or an RNA with modified nucleotides. Suitable RNases include, for example, RNase-A and RNase-H. In some embodiments, the treatment can include using a combination of two or more RNases, if desired. The RNase treatment can improve downstream end repair and end modification reactions.

In embodiments in which the digestible adapter is digested with treatment with a glycosylase that can degrade specific nucleotides such as dUTP in single-stranded RNA, double-stranded RNA, a RNA-DNA hybrid, a RNA-DNA hetero-duplex, an RNA with modified nucleotides, DNA with modified nucleotides, or any other modified oligonucleotides such as LNA or PNA.

Figure 8:
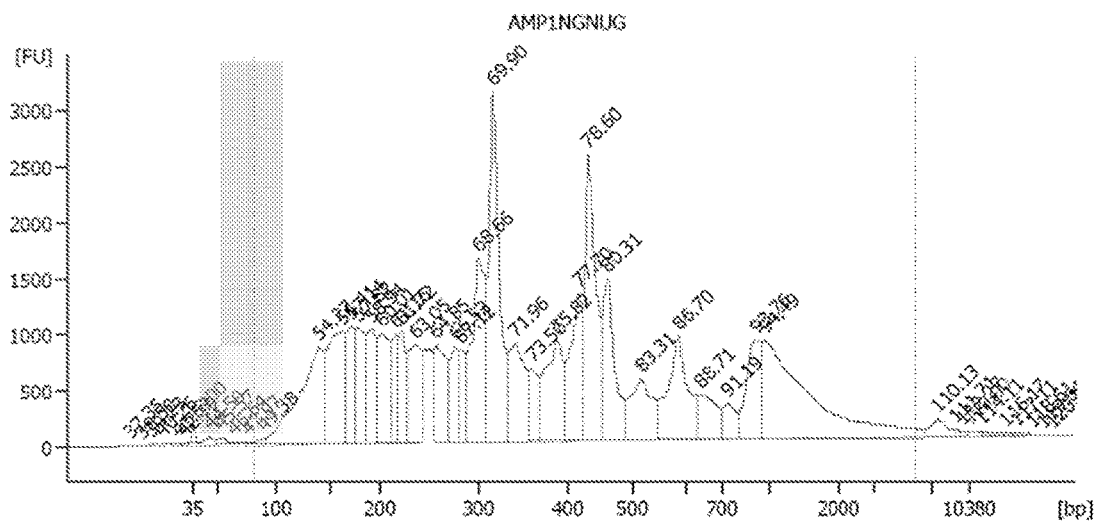
FIG. 8. Comparison of existing protocol versus the methods described herein for amplification using 1 ng of total RNA as template. (A) Agilent DNA high sensitivity labchip assay profile of RNA amplification product using OVATION RNA-seq system V2 (NuGEN Technologies, Inc., San Carlos, Calif.). The minimum fragment size seen is approximately 100 bp. (B) similar profile of product of RNA amplification using the method described herein. Fragments of 30 nucleotides (including adapters) and above were detected, confirming the amplification and recovery of both small and long RNAs in same amplification procedures. Shaded boxes highlight the region that is amplified only when using the methods described herein.
Figure 8:
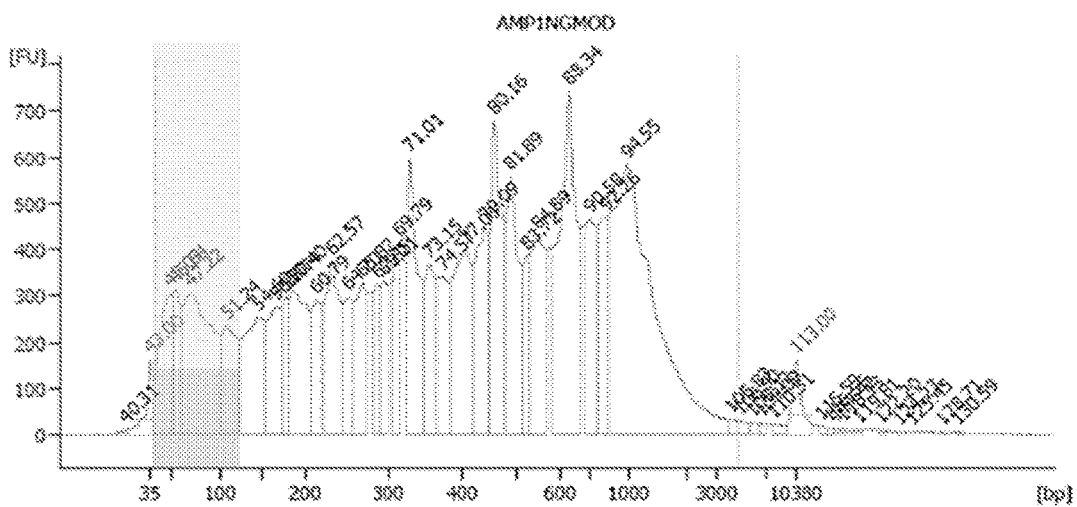
Figure 9:
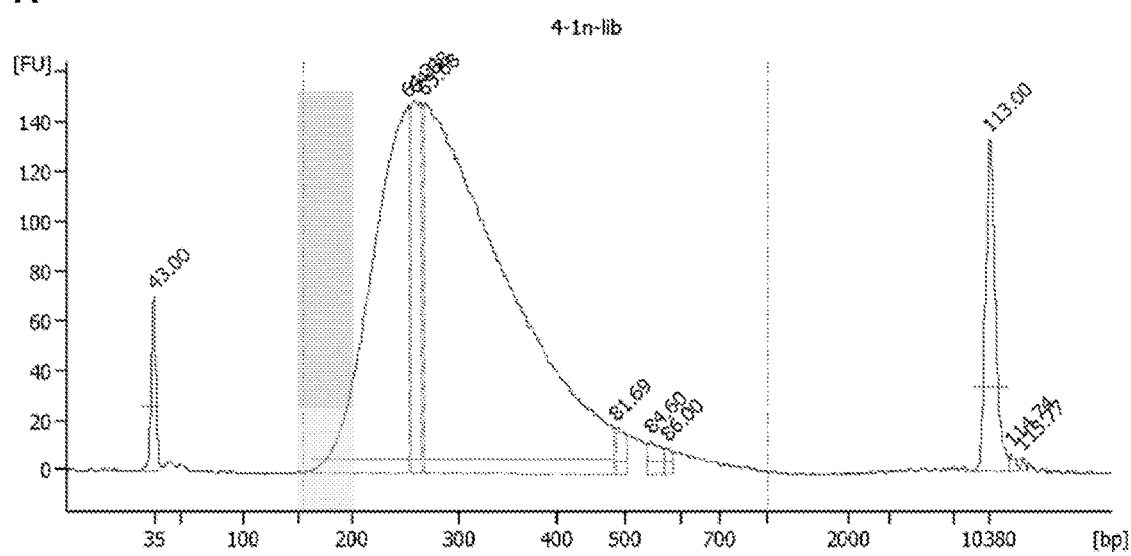
FIG. 9. Comparison of library prepared from a cDNA template (the product of RNA amplification using 1 ng RNA as template) using an existing protocol versus the methods described herein. (A) Agilent DNA high sensitivity labchip assay profile of RNA amplification product using OVATION RNA-seq system V2 (NuGEN Technologies, Inc., San Carlos, Calif.). The minimum fragment size seen is approximately 200 bp. (B) Similar profile of product of RNA amplification using the methods described herein. Fragments of approximately 150 bases (including approximately 30 nucleotides of amplified product and 120 nucleotides of adapters) and above were detected, confirming the library prepared consists of both small and long RNAs in the same library preparation procedures. Shaded boxes highlight the region that is amplified only when using the methods described herein.
Figure 9:
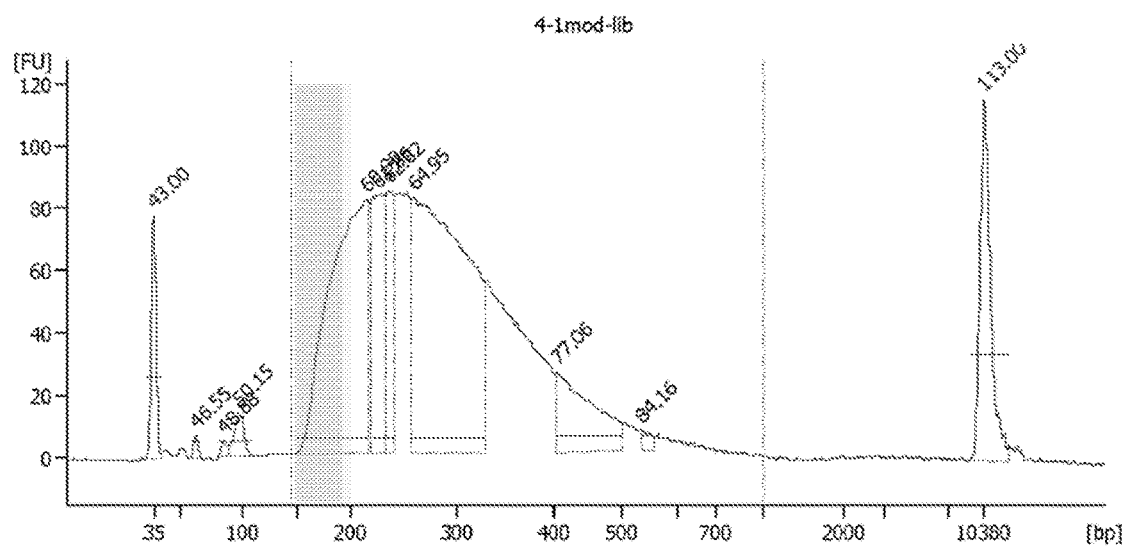

An Agilent high sensitivity DNA assay chip analysis shows recovery of all fragments above 30 nucleotides in length (FIG. 1B). FIG. 1A, shows the profile obtained using an OVATION RNA-Seq System V2 (NuGEN Technologies, Inc., San Carlos, Calif.) kit without using the modified protocol as described above. A comparison of FIG. 1A to FIG. 1B, FIG. 7A to FIG. 7B, and/or FIG. 8A to FIG. 8B reveals that the methods described herein can amplify all RNAs larger than 15 nucleotides effectively, including small RNAs and, in particular, small RNAs having 75 nucleotides or fewer.

Figure 2:
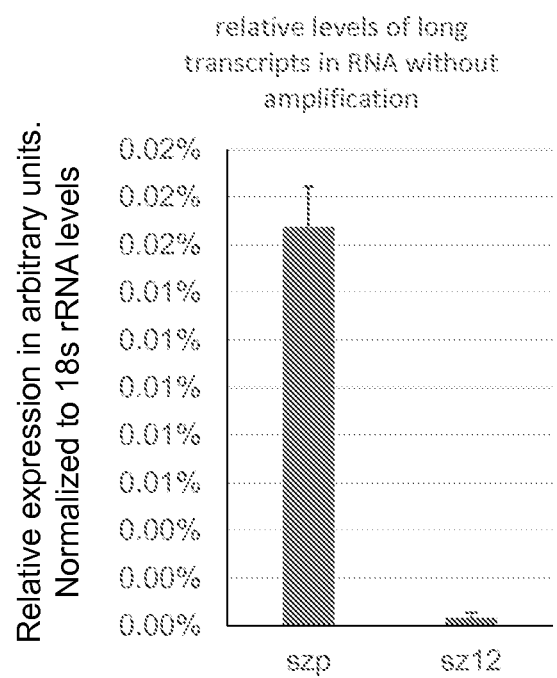
FIG. 2. Comparison of expression of longer RNAs by semi-quantitative real-time PCR in libraries prepared using unamplified RNA and amplified RNA product as templates. (A) SUZ12P transcript levels are high in HEK293-T cells compared to SUZ12 gene. (B) Data showing similar trend in levels of SUZ12P and SUZ12. This indicates efficient and proportionate amplification and library preparation of long RNAs.
Figure 2:
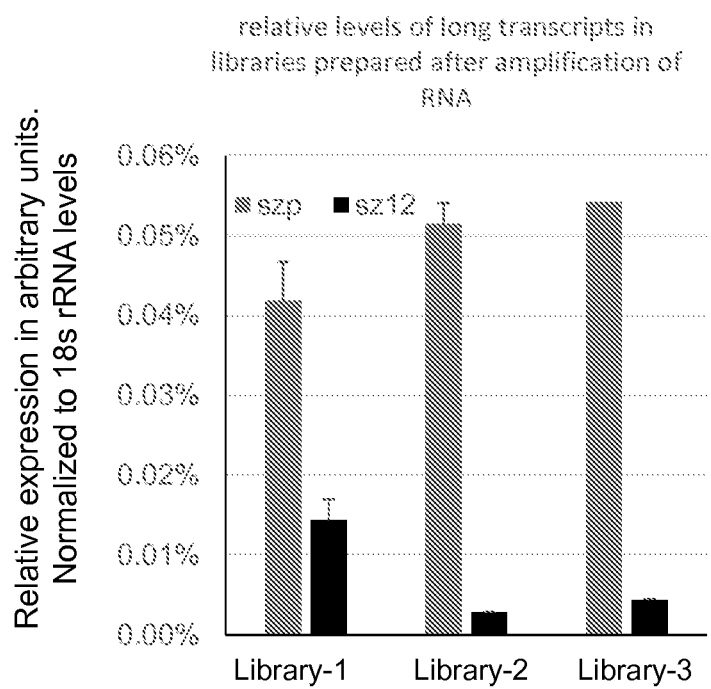
Figure 3:
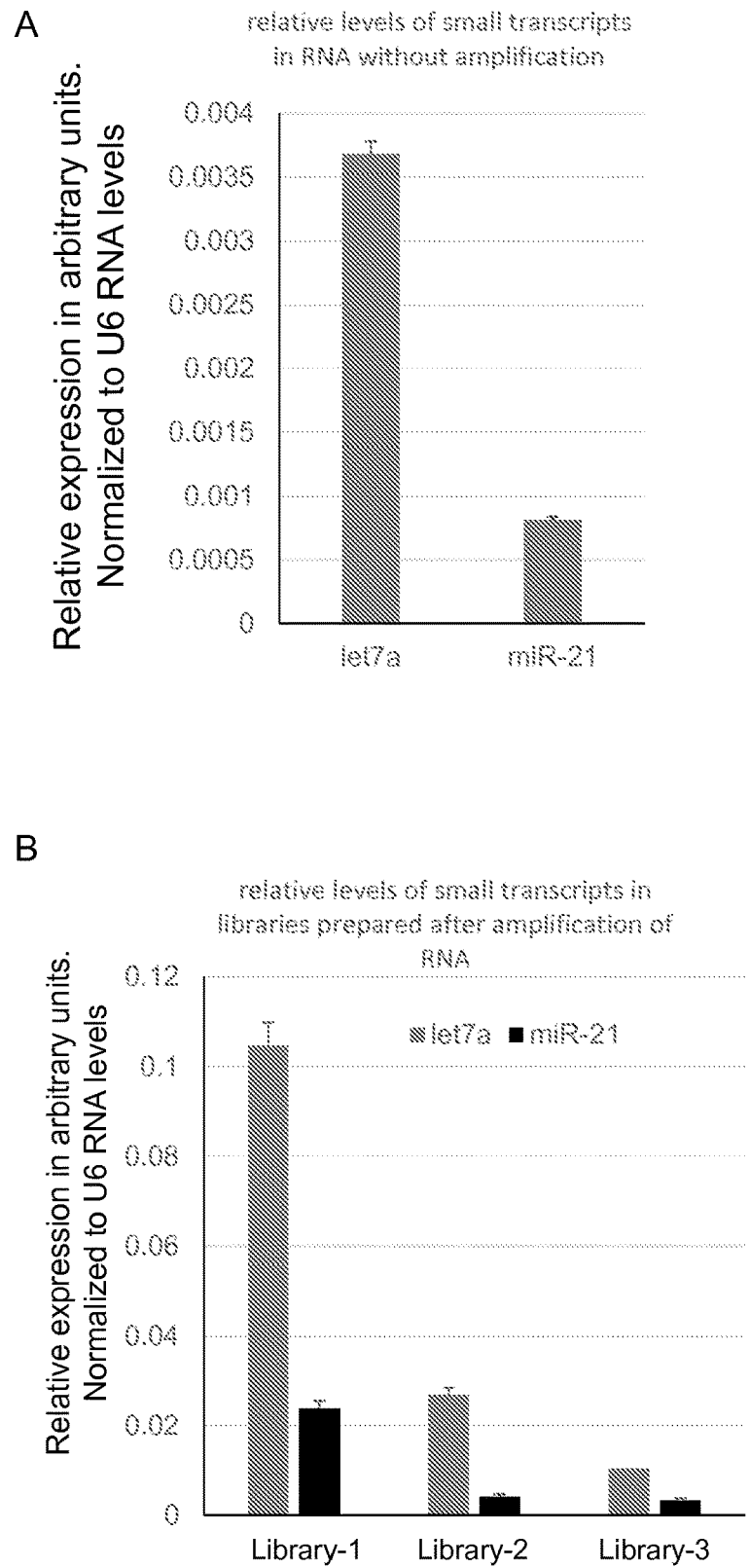
FIG. 3. Comparison of expression of small RNAs by semi-quantitative real-time PCR in libraries prepared using unamplified RNA and amplified RNA product as template. (A) let7a levels are relatively high compared to miR21 in HEK-293T cells. (B) Data showing a similar trend in expression of these miRNAs (let7a and miR-21). This indicates efficient and proportionate amplification and library preparation of small RNAs.
Figure 4:
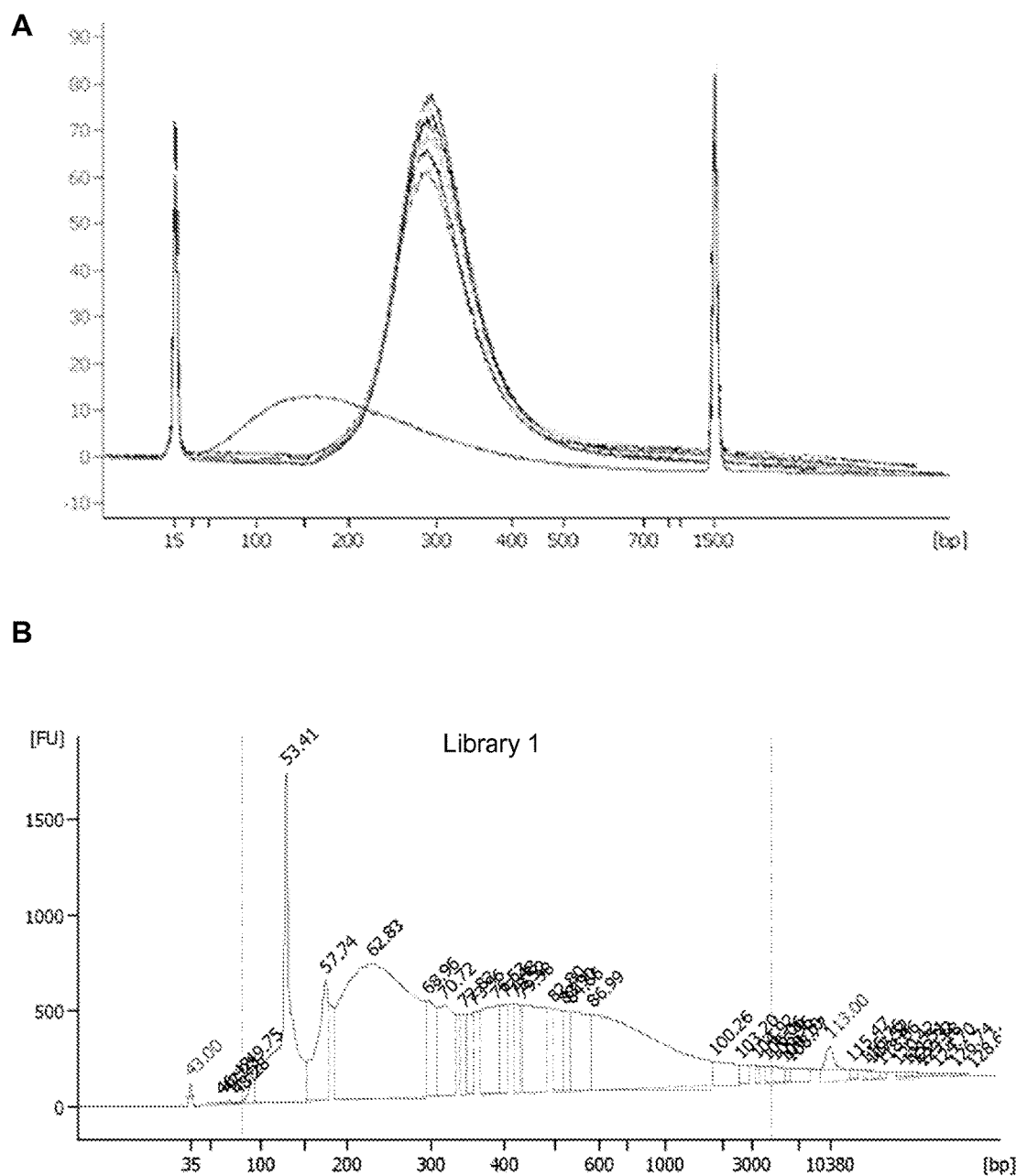
FIG. 4. Comparison of existing methods and our modified methods of sequencing library preparation. (A) Agilent DNA bioanalyser chip 1000 profile of library prepared using Ovation Ultralow DR Multiplex system (NuGEN Technologies, Inc., San Carlos, Calif.) shows a peak at approximately 300 bp indicating an average size of the fragment inserted into library is approximately 150-200 bp. (B-D) Profiles of libraries prepared using methods described herein show peaks starting from approximately 150 bp, indicating incorporation of fragments of approximately 30 bp and above.
Figure 4:
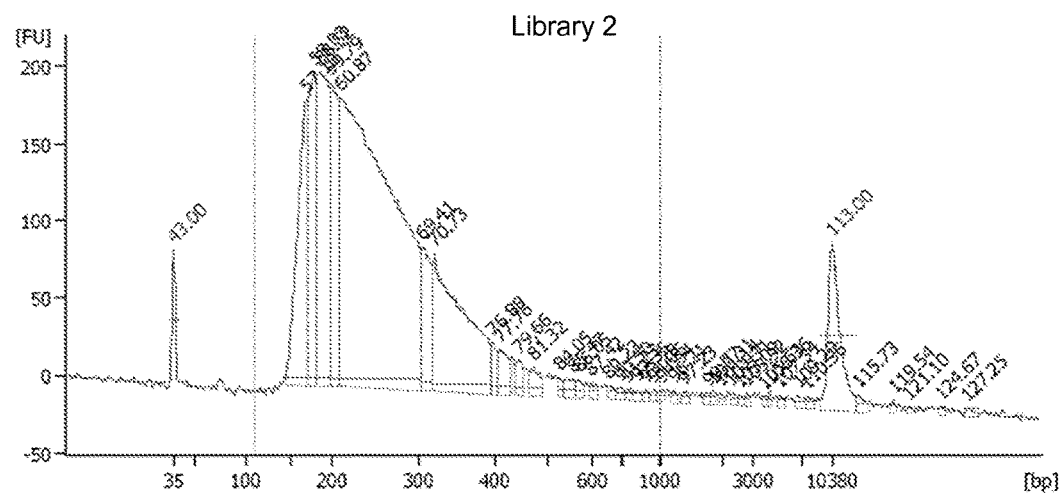
Figure 4:
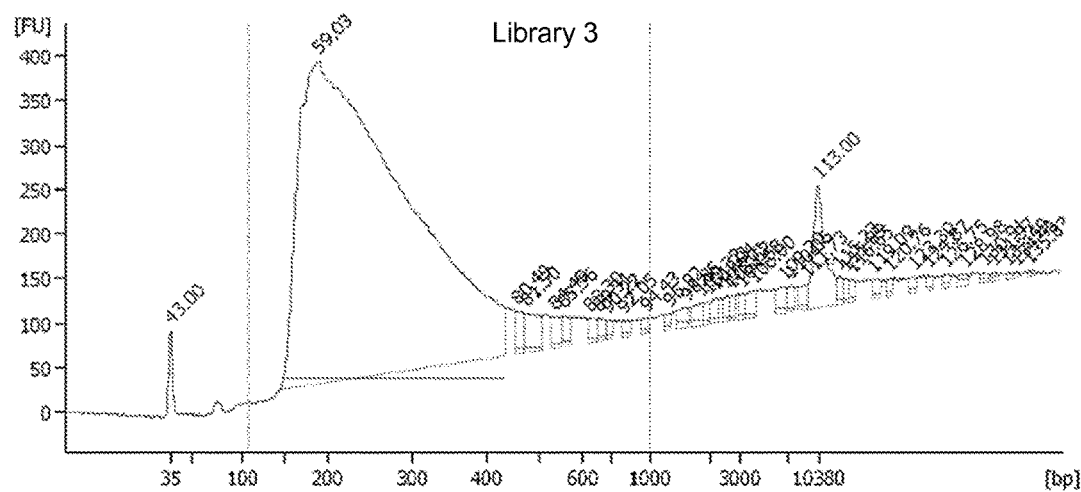

FIG. 2 and FIG. 3 provide confirmation that the methods described herein can provide proportionate amplification without bias for size or sequence. FIG. 2 shows the expression profiles of longer transcripts SUZ12 and SUZ12P1. Levels of these transcripts were compared between unamplified RNA and product of RNA amplification. FIG. 2 shows good correlation between amplified and unamplified RNAs confirming negligible bias. FIG. 3 shows the expression profiles of smaller transcripts miRNAs let7a and miR-21.

Library Preparation

Amplified RNA can be profiled after being converted into a library compatible with high throughput sequencing, RT-PCR, or microarray-based experiments. Conventional library preparation methods may be modified to further include the isolation procedure and/or the adapter digesting treatment described above to generate a library of amplified RNA product suitable for use in many analytical assays including, for example, first, second, and third generation sequencing platforms (e.g., Illumina, Solid, and Pyro-Sequencing), other quantitative and semi-quantitative methods (e.g., various PCR methods), and blotting methods. As used herein, the term "library" refers to a set of products that may vary with respect to length, nucleotide sequence, and/or modifications.

The methods described herein can capture fragments of RNA and/or DNA—and thus produce a library that includes amplified RNA products—as small as 15 bp. In some embodiments, the RNA template can be amplified into DNA. Such amplified fragments corresponding to RNA fragments of 15 bases were also captured. The RNA amplification modifications can efficiently incorporate more fragments and fragments of various lengths (15 bp and above) into a library so that the library is compatible with high throughput sequencing by second generation sequencing methods and PCR (FIGS. 2-4 and 9).

The library preparation methods described herein can be performed on any suitable polynucleotide template. Exemplary suitable templates include single-stranded RNA or DNA, double-stranded DNA or RNA, double-stranded DNA or RNA fragments, or double-stranded DNA-RNA hybrids. As used herein, the term "double-stranded" refers to at least a portion of the template and does not require that each and every base on one strand has a complementary base on the other strand, and therefore includes templates that may otherwise be characterized as "partially double-stranded." In many cases, the template may be an amplified polynucleotide.

So, for example, a conventional library preparation kit may involve shearing a polynucleotide template (e.g., an amplified polynucleotide). The polynucleotide template may be treated with an RNase or a glycosylase before or after being sheared. The RNase treatment can include treating the amplified product, regardless of whether the amplified product is at least partially isolated, with any RNase that can degrade RNA in single-stranded RNA, double-stranded RNA, a RNA-DNA hybrid, a RNA-DNA hetero-duplex, or an RNA with modified nucleotides. Suitable RNases include, for example, RNase-A and RNase-H. In some embodiments, the treatment can include using two or more RNases, if desired. Glycosylase treatment can include treatment with a DNA glycosylase such as, for example, a uracil-DNA-glycosylase.

Standard library preparation protocols typically further include steps in which the sheared ends of the template polynucleotide are repaired and/or ligated to an adapter. Standard library preparation protocols typically further include steps in which the library is amplified. The methods described herein involve modifying standard protocols by including an isolation step similar to that described above in connection with amplifying the RNA template. The sheared polynucleotide, the ligation product, and/or the amplified library can be isolated using carboxylated magnetic beads in presence of NaCl (or analogous salt such as, for example, KCl), $MgCl_2$ (or analogous salt such as, for example, $MgSO_4$ or $(CH_3COO)_2Mg$), polyethylene glycol (PEG, e.g., PEG-8000), ethanol, and/or isopropanol, and/or isobutanol either alone or in combinations. The particular conditions can depend, at least in part, on the components of earlier reaction buffers, other components of reaction, reaction products and templates.

If more than one isolation is performed, each isolation may be designed independently of the others—i.e., using different combinations of isolation composition components.

FIG. 3 shows a semi-quantitative real time PCR profiling of two microRNAs: let7a and miR21. We compared the levels of these micro RNAs between unamplified RNA and the library prepared by using the same RNA as template—total RNA was first amplified using the amplification methods described herein and then a library was prepared using the methods described immediately above. FIG. 3 show good correlation between the trend in expression of both miRNAs, confirming negligible bias and effective recovery of smaller RNA specific fragments.

FIG. 4A and FIG. 9A reflects expression profile data generated by analyzing a library prepared using a conventional library preparation kit (Ovation Ultralow DR multiplex library system, NuGEN Technologies, Inc., San Carlos, Calif.). FIG. 4B and FIG. 9B shows a library prepared using our modified protocol, which is effective in recovering all fragments from 150 bp and larger. Since the adapters used in the ligation step of the library preparation protocol amounted to approximately 120 bases, a library fragment of 150 bases reflects an amplified RNA product of 30 bases. A comparison of FIG. 4A versus FIG. 4B and/or FIG. 9A versus FIG. 9B shows that our modifications can allow (a) isolation of smaller fragments, reflecting amplification of small RNAs and incorporating those small RNAs into the library, and (b) a broader distribution of the size of RNA templates that are incorporated into the library.

Figure 5:
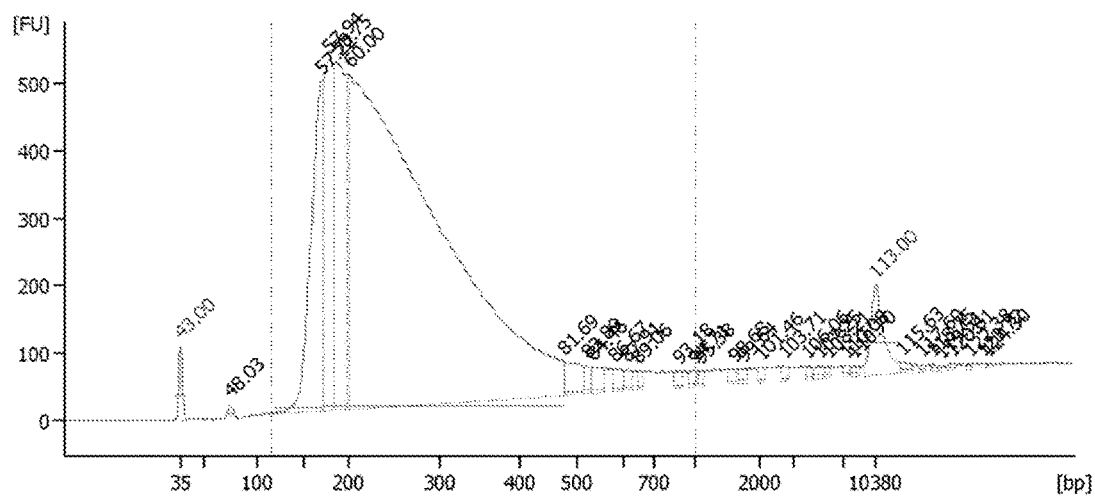
FIG. 5. Comparison of Agilent DNA high sensitivity assay profiles of libraries prepared with RNase treated and untreated templates. Two nanograms of RNA of HEK-293T cells were amplified and the amplified product was sheared. 10 ng of sheared and purified product, either with (B) or without (A) RNase treatment, was used for making libraries. (A) Profile of library prepared without an additional RNase treatment. (B) Profile of library prepared with an additional RNase treatment.
Figure 5:
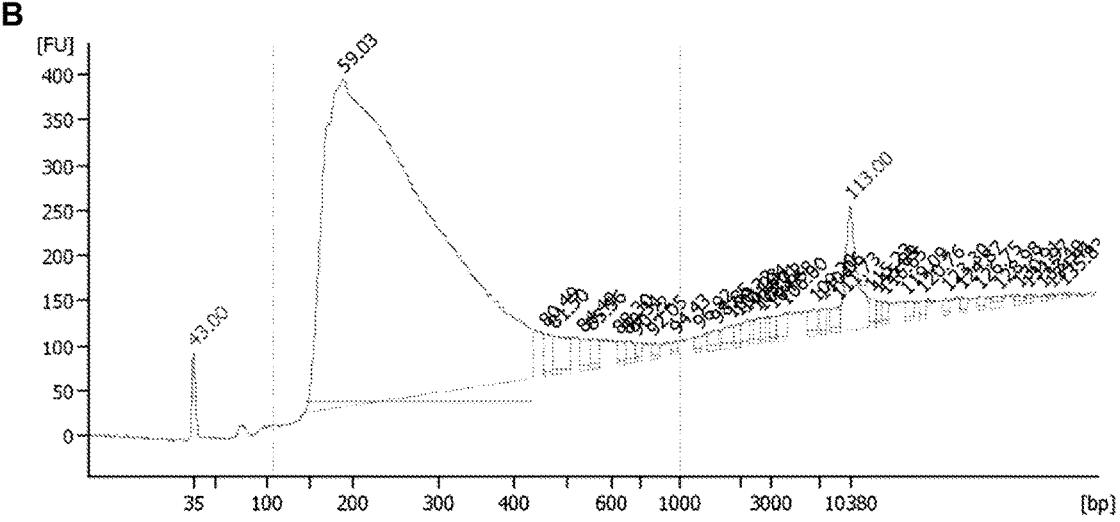

FIG. 5 B shows that RNase treatment increases the efficiency of library preparation. The increased breadth and intensity of peaks in RNase-treated samples reflect higher efficiency of incorporation of smaller fragments—i.e., fragments harboring amplifications of small RNAs—into library preparations compared to libraries prepared without RNase treatment.

Figure 6:
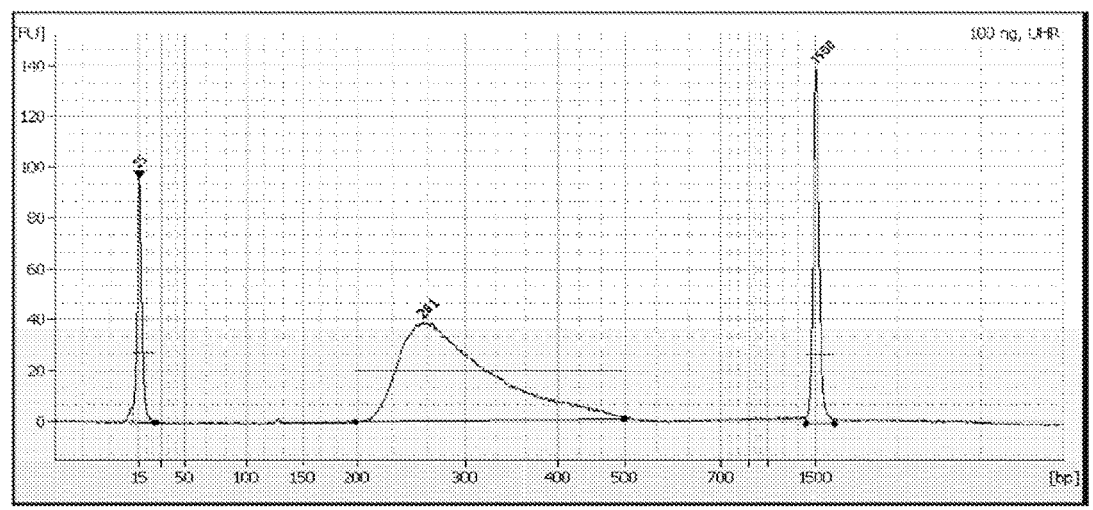
FIG. 6. Comparison of existing methods of sequencing library preparation and methods described herein. (A) Agilent DNA-1000 chip profile of library prepared using TRUSEQ RNA Sample Preparation v2 kit (Illumina, Inc., San Diego, Calif.) shows a peak at 260 bp indicating an average size of the fragment inserted into library is approximately 100 bp. (B) Profile of library prepared using methods described herein shows broader peaks starting from 120 bases indicating efficient incorporation of fragments of 15 bp and above.
Figure 6:
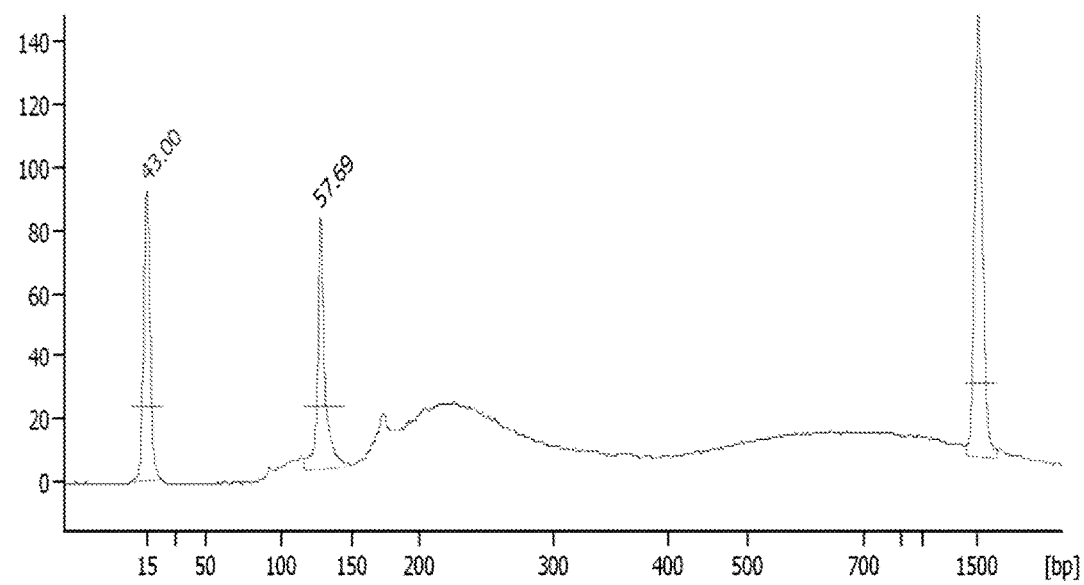
Figure 7:
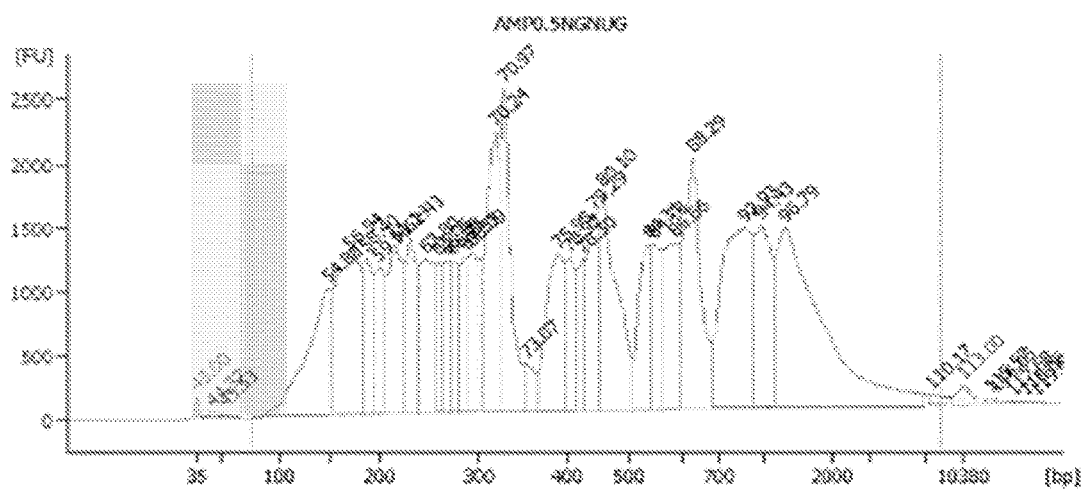
FIG. 7. Comparison of existing protocol versus the methods described herein for amplification using 500 pg of total RNA as template. (A) Agilent DNA high sensitivity labchip assay profile of RNA amplification product using OVATION RNA-seq system V2 (NuGEN Technologies, Inc., San Carlos, Calif.). The minimum fragment size seen is approximately 100 bp. (B) Similar profile of product of RNA amplification using the method described herein. Fragments of approximately 30 nucleotides (including adapters) and above were detected, confirming the amplification and recovery of both small and long RNAs in same amplification procedures. Shaded boxes highlight the region that is amplified only when using the methods described herein.
Figure 7:
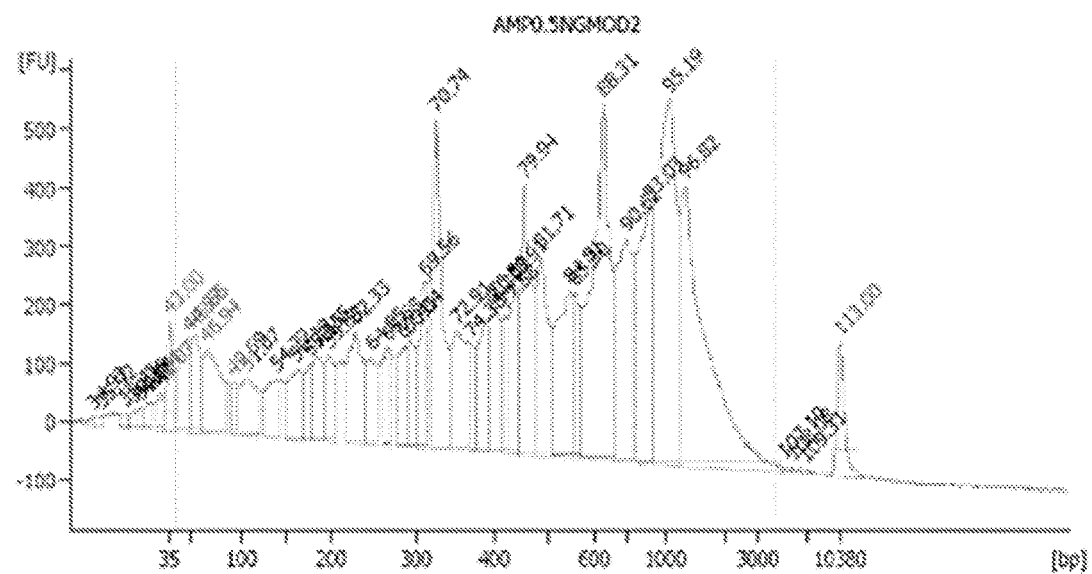

FIG. 6 reflects expression profiles data generated by analyzing a library prepared using an alternative conventional library preparation kit (TruSeq RNA Sample Preparation Kit v2, Illumina, Inc., San Diego, Calif.). FIG. 6A reflects a library prepared according to the manufacturer's instructions, with no additional isolations or RNase treatments. The data show a peak at approximately 260 bases, which reflects incorporation of fragments more than approximately 100 bp in length (adapters together amount to approximately 120 bases). FIG. 6B shows the profile of library prepared using our protocol and the peaks are broad relative to the peaks in FIG. 6A and start at approximately 120 bases. It is evident that our modifications can result in amplified fragments of small RNAs being efficiently incorporated into libraries.

Combined, therefore, this disclosure describes a complete set of methods that enable one to profile small RNAs from a very low quantity of template RNA. Compared to existing technologies, our methods can incorporate amplified RNA into a library with higher efficiency. Moreover, our method can efficiently incorporate smaller fragments with very little bias compared to existing technologies. Our amplification method can amplify both small RNA and long RNAs together in the same reaction. As used herein, the term "long RNA" refers to an RNA having more than 200 bases. The amplification product—whether RNA or DNA—can be made into a library for further analysis using our library preparation method. This is a significant improvement over technologies that require small RNAs and large RNAs to be amplified and profiled in separate experiments. Our methods therefore allow one to reduce the quantity of template required to analyze expression of both small RNAs and large RNAs from a single sample. Of course, our methods are fully compatible with amplifying and/or preparing a library from small RNAs, long RNAs, and/or any RNA template fractionated based on, for example, size.

Another feature of our methods is that they may be performed independent of modifying the ends of the RNA before being incorporated into a library. Many amplification and library preparation kits perform end-modification of RNAs first and then incorporate the modified RNAs into a library. When using these protocols, however, end modifications reactions may not be complete, one may not understand all possible natural modification to RNAs, and/or the RNAs may not be suitably modified to be incorporated into the library. Therefore, one may lose information about unknown RNAs with uncharacterized modifications.

This disclosure therefore describes an approach independent of end modifications. The methods described herein are, however, compatible with both end-modification-based and end-modification-independent approaches to amplify all RNAs and it can detect all such RNAs more efficiently.

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

RNA Amplification 2 ng RNA from human brain and 2 ng universal human reference was used to amplify using OVATION RNA-Seq System V2 (NuGEN Technologies, Inc., San Carlos, Calif.) (adapted from FIG. 3 of user guide of the product)(FIG. 1A). 2 ng of Total RNA isolated from HEK-293T cells was used to amplify using our modified protocol (FIG. 1B). FIG. 2 shows expression profile of long RNAs (eg., SUZ12 and SUZ12P) and FIG. 3 shows expression profile of small RNAs (e.g., miR21 and let-7a) using the library prepared from amplified product.

The first strand cDNA synthesis and second strand cDNA synthesis was performed according to the manufacturer's instructions.

The product of the second strand cDNA synthesis was isolated using carboxyl magnetic beads (Agencourt RNA-Clean XP, Beckman Coulter, Inc., Brea, Calif.) using a ratio of carboxyl magnetic beads between 1- to 2-fold.

A mixture of NaCl (10 mM), $MgCl_2$ (20 mM), PEG 8000 (5%), and ethanol 37%) was added and incubated at room temperature for 5-10 minutes to allow second strand synthesis product to bind to the magnetic beads. The beads were collected using a magnetic plate according to conventional protocols. The magnetic beads were washed three times using 70-80% ethanol, then dried.

The beads were resuspended in nuclease free water for 5-10 minutes to recover the DNA/RNA from the magnetic beads and the supernatant collected. The isolated products of second strand cDNA synthesis were used for single primer isothermal amplification (OVATION RNA-Seq System V2, NuGEN Technologies, Inc., San Carlos, Calif.), performed according to the manufacturer's protocol. The amplification product was isolated using the isolation procedure described above.

The isolated product was treated with RNase H using manufacturer protocol (New England Biolabs, Inc., Ipswich, Mass.).

Example 2

2 ng of RNA from HEK-293T cells was used to amplify RNA. The product of amplification is double stranded DNA. The amplified product was, sheared, treated with RNase H, and isolated. This isolated product was used as template for preparation of library.

The RNA was amplified as described in Example 1. The amplified product was sheared using Covaris S-series Sonication System (Covaris, Inc., Woburn, Mass.) according to manufacturer's instructions. The sheared material was treated with RNase H as described in Example 1.

A library was constructed using the isolated product and Ovation Ultralow DR multiplex System (NuGen Technologies, Inc., San Carlos, Calif.) according to manufacturer's instructions. The ligation products were again isolated using carboxylated magnetic beads in presence of 37% ethanol.

The isolated library was amplified using the Ovation Ultralow DR multiplex System (NuGen Technologies, Inc., San Carlos, Calif.) according to the manufacturer's instructions. The isolated library was subjected to standard qualitative and quantitative analyses.

Example 3

Template was amplified, sheared, isolated, and treated with RNase as described in Example 2.

A library was constructed using the isolated product and TruSeq RNA Sample Preparation Kit (v2, Illumina, Inc., San Diego, Calif.) according to the manufacturer's instructions.

The library was isolated as described in Example 2, then subjected to standard qualitative and quantitative analyses.

Results are shown in FIG. 6.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

As used herein, the term "and/or" means one or all of the listed elements or a combination of any two or more of the listed elements; the terms "comprises" and variations thereof do not have a limiting meaning where these terms appear in the description and claims; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method of amplifying an RNA template, the method comprising:
    annealing a primer to the RNA template, the primer comprising:
        a region complementary to a portion of the RNA template; and
        a digestible oligonucleotide adapter comprising RNA, DNA, an RNA/DNA hybrid, LNA, PNA, an oligonucleotide comprising at least one modified nucleotide, at least a portion of a plasmid, or at least a portion of a virus;
    synthesizing an oligonucleotide from the primer, thereby producing a product that comprises a nucleotide strand complementary to the RNA template having the digestible oligonucleotide adapter;
    isolating at least a portion of the oligonucleotide; and
    subjecting the isolated product to treatment that digests at least a portion of the digestible adapter but does not digest the nucleotide strand complementary to the RNA template.

2. The method of claim 1 wherein the oligonucleotide comprises RNA, dsDNA, cDNA, partially double stranded RNA, partially double stranded DNA, or an RNA-DNA hybrid.

3. The method of claim 1 wherein isolating at least a portion of the oligonucleotide comprises performing isothermal amplification on at least a portion of the isolated oligonucleotide; and
    isolating at least a portion of the isothermal amplification product, thereby producing the isolated product for treatment that digests at least a portion of the digestible adapter.

4. The method of claim 1 wherein isolating a portion of the oligonucleotide comprises incubating at least a portion of the oligonucleotide in a composition that comprises NaCl or KCl.

5. The method of claim 1 wherein isolating a portion of the oligonucleotide comprises incubating at least a portion of the oligonucleotide in a composition that comprises $MgCl_2$, $MgSO_4$, or $(CH_3COO)_2Mg$.

6. The method of claim 1 wherein isolating a portion of the oligonucleotide comprises incubating at least a portion of the oligonucleotide in a composition that comprises polyethylene glycol.

7. The method of claim 1 wherein isolating a portion of the oligonucleotide comprises incubating at least a portion of the oligonucleotide in a composition that comprises ethanol.

8. The method of claim 1 wherein isolating a portion of the oligonucleotide comprises incubating at least a portion of the oligonucleotide in a composition that comprises isopropanol.

9. The method of claim 1 wherein the treatment that digests at least a portion of the digestible adapter comprises treatment with an RNase.

10. The method of claim 9 wherein the RNase comprises RNase-A or RNase-H.

11. The method of claim 1 wherein the treatment that digests at least a portion of the digestible adapter comprises treatment with a glycosylase.

12. The method of claim 11 wherein the glycosylase comprises uracil-DNA glycosylase.

13. The method of claim 1 wherein the treatment that digests at least a portion of the digestible adapter comprises physical or chemical digestion of the isolated product.

14. The method of claim 1 wherein isolating at least a portion of the oligonucleotide comprises contacting at least a portion of the oligonucleotide with a carboxylated magnetic bead.

15. The method of claim 1, wherein the treatment that digests at least a portion of the digestible adapter excludes digestion using an endonuclease or an exonuclease.

* * * * *